US012594125B2

(12) United States Patent
Palushi et al.

(10) Patent No.: US 12,594,125 B2
(45) Date of Patent: Apr. 7, 2026

(54) VISUALIZATION SYSTEM AND METHOD FOR ENT PROCEDURES

(71) Applicants: Acclarent, Inc., Irvine, CA (US); Biosense Webster (Israel) Ltd., Yokneam (IL)

(72) Inventors: Jetmir Palushi, Irvine, CA (US); Itamar Bustan, Zichron Ya'acov (IL); Noam Racheli, Hadera (IL); Itzhak Fang, Irvine, CA (US); Athanasios Papadakis, Newport Beach, CA (US); Vadim Gliner, Haifa (IL)

(73) Assignees: Acclarent, Inc., Irvine, CA (US); Biosense Webster (Israel) Ltd., CA Yokneam (IL)

( * ) Notice: Subject to any disclaimer, the term of this patent is extended or adjusted under 35 U.S.C. 154(b) by 595 days.

(21) Appl. No.: 17/037,809

(22) Filed: Sep. 30, 2020

(65) Prior Publication Data

US 2021/0121238 A1     Apr. 29, 2021

Related U.S. Application Data

(60) Provisional application No. 62/925,441, filed on Oct. 24, 2019.

(51) Int. Cl.
*A61B 34/20*        (2016.01)
*A61B 90/00*        (2016.01)
(Continued)

(52) U.S. Cl.
CPC .............. *A61B 34/20* (2016.02); *A61B 90/37* (2016.02); *A61B 17/24* (2013.01);
(Continued)

(58) Field of Classification Search
CPC ......... A61B 34/20; A61B 90/37; A61B 17/24; A61B 2034/107; A61B 2034/2055;
(Continued)

(56) References Cited

U.S. PATENT DOCUMENTS

| | | | |
|---|---|---|---|
| 7,720,521 B2 | 5/2010 | Chang et al. | |
| 10,463,242 B2 | 11/2019 | Kesten et al. | |

(Continued)

FOREIGN PATENT DOCUMENTS

WO      WO 2018/203304 A1     11/2018

OTHER PUBLICATIONS

International Search Report and Written Opinion dated Jan. 25, 2021, for International Application No. PCT/IB2020/059863, 14 pages.

*Primary Examiner* — Kaitlyn E Sebastian
(74) *Attorney, Agent, or Firm* — Barnes & Thornburg LLP

(57)        ABSTRACT

A visualization system may be implemented with an image guided surgery navigation system for use during ENT procedures. Correlated datasets such as surgical paths and pre-operative image slices may be correlated with the coordinate system of the navigation system for reference during a procedure. A surgeon may wear a head mounted display ("HMD") having a transparent screen through which the patient anatomy may be viewed. The orientation and distance of the head mounted display relative to the patient anatomy may be determined using magnetic position tracking, image analysis of images captured by a camera of the HMD, or both. Correlated datasets may then be transformed based on the relative distance and orientation and may be displayed via the transparent screen to overlay directly viewed patient anatomy. Some implementations may include optical fiducials integrated with a patient tracking (Continued)

101

IGS Navigation System
10

Patient Tracker
50

100

60 assembly to aid in tracking the patient and determining perspective of the HMD.

15 Claims, 9 Drawing Sheets

(51) Int. Cl.

| | | |
|---|---|---|
| *A61B 17/24* | (2006.01) | |
| *A61B 34/10* | (2016.01) | |
| *A61B 90/50* | (2016.01) | |

(52) U.S. Cl.
CPC . *A61B 2034/107* (2016.02); *A61B 2034/2051* (2016.02); *A61B 2034/2055* (2016.02); *A61B 2090/365* (2016.02); *A61B 2090/373* (2016.02); *A61B 2090/374* (2016.02); *A61B 2090/3762* (2016.02); *A61B 2090/378* (2016.02); *A61B 2090/3937* (2016.02); *A61B 2090/3983* (2016.02); *A61B 2090/502* (2016.02)

(58) Field of Classification Search
CPC ........ A61B 2090/365; A61B 2090/373; A61B 2090/3937; A61B 2090/3983; A61B 2090/502; A61B 2034/2051; A61B 2090/374; A61B 2090/3762; A61B 2090/378; A61B 2034/105; A61B 2034/2048; A61B 2034/2072; A61B 2034/256; A61B 2090/372
See application file for complete search history.

(56) References Cited

U.S. PATENT DOCUMENTS

| | | | | |
|---|---|---|---|---|
| 10,561,370 | B2 | 2/2020 | Salazar et al. | |
| 10,888,382 | B2 | 1/2021 | Ngo-Chu et al. | |
| 2002/0156363 | A1* | 10/2002 | Hunter | G06T 3/14 |
| | | | | 600/410 |
| 2011/0043616 | A1* | 2/2011 | Dobbie | G02B 27/017 |
| | | | | 348/333.08 |
| 2014/0276004 | A1* | 9/2014 | Strupeck | H05K 1/189 |
| | | | | 600/424 |
| 2014/0364725 | A1 | 12/2014 | Makower | |
| 2017/0042631 | A1* | 2/2017 | Doo | H04N 13/398 |
| 2017/0299860 | A1* | 10/2017 | Wall | G02B 3/04 |
| 2018/0185113 | A1* | 7/2018 | Gregerson | A61B 34/35 |
| 2019/0183582 | A1* | 6/2019 | Ngo-Chu | A61B 90/361 |
| 2019/0223958 | A1* | 7/2019 | Kohli | A61B 8/4427 |
| 2019/0282305 | A1* | 9/2019 | Shameli | A61B 17/00234 |
| 2019/0374290 | A1* | 12/2019 | Stolka | A61B 90/39 |
| 2019/0388157 | A1* | 12/2019 | Shameli | A61B 17/32002 |
| 2021/0220068 | A1* | 7/2021 | Kim | A61B 17/00234 |

* cited by examiner

101

IGS Navigation
System
10

Patient Tracker
50

100

60

100

108    106    104    102

| Perspective Sensor 110 | Communication Device 112 | Processor & Memory 114 | Power Source 116 |
|---|---|---|---|

VISUALIZATION SYSTEM AND METHOD FOR ENT PROCEDURES

PRIORITY

This application claims priority to U.S. Provisional Pat. App. No. 62/925,441, entitled "Visualization System and Method for ENT Procedures," filed Oct. 24, 2019, the disclosure of which is incorporated by reference herein.

BACKGROUND

Image guided surgery navigation systems are used during surgical procedures to provide additional information and visual perspectives of a surgical site or other patient anatomy. This may include displaying pre-operative images (e.g., CT images) of the surgical site from various perspectives, and may also include overlaying markers onto such displayed images to indicate static information, such as a planned path that a surgical instrument will take during a procedure, as well as dynamic information, such as the present location of a distal tip of the surgical instrument. Such information may be used to improve the accuracy and safety with which a surgical instrument is navigated to a particular location within a patient's body.

Given the breadth of additional information available during image guided surgery, a surgeon or other practitioner may sometimes become spatially disoriented while switching between views of the surgical site, or while switching between direct viewing of the patient anatomy and viewing of simulated images of the patient anatomy. For example, in some cases a surgeon may be viewing a CT slice of an axial view of the patient's head on a display of the image guided surgery navigation system, while also occasionally viewing the patient's head directly. In such cases, the surgeon may become disoriented and unable to determine the spatial and directional correspondence between their direct perceptions and the axial view, which may lead to erroneous movements of the surgical instrument within the patient's head.

While several systems and methods have been made and used in ear, nose, and throat ("ENT") procedures, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
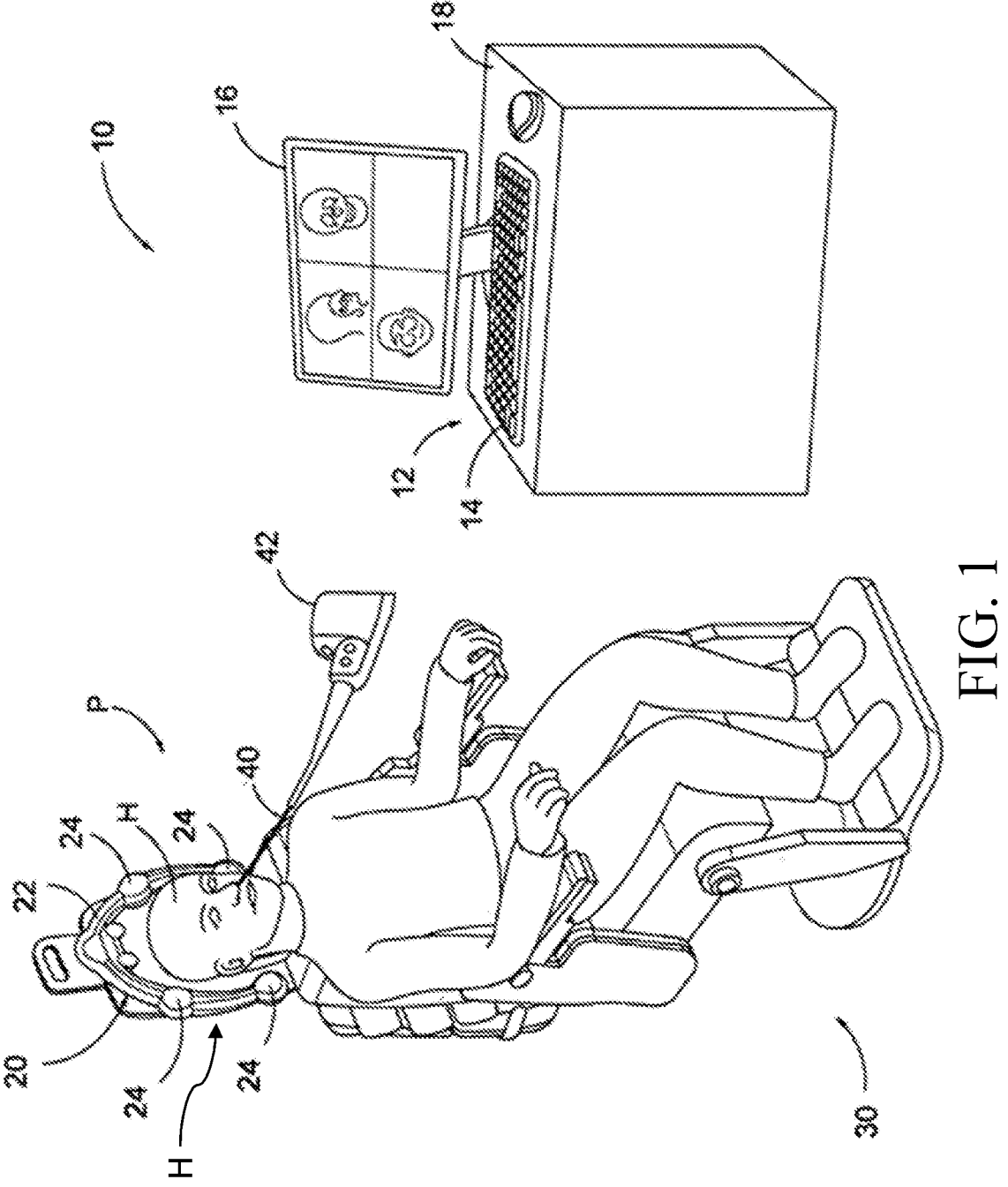
FIG. 1 depicts a schematic view of an exemplary surgery navigation system being used on a patient seated in an exemplary medical procedure chair.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Image Guided Surgery Navigation System

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P) to produce a tracked area that the IGS navigation system (10) associates a coordinate system with. A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. Pat. No. 10,561,370, entitled "Apparatus to Secure Field Generating Device to Chair," issued Feb. 18, 2020, the disclosure of which is incorporated by reference herein.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from navigation guidewire (40) to determine the location of a sensor in navigation guidewire (40) within the head (H) of the patient (P). Processor (12) comprises a processing unit (e.g., a set of electronic circuits arranged to evaluate and execute software instructions using combinational logic circuitry or other similar circuitry) communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Navigation guidewire (40) includes a sensor (not shown) that is responsive to positioning within the alternating magnetic fields generated by field generators (24). A coupling unit (42) is secured to the proximal end of navigation guidewire (40) and is configured to provide communication of data and other signals between console (18) and navigation guidewire (40). Coupling unit (42) may provide wired or wireless communication of data and other signals.

In the present example, the sensor of navigation guidewire (40) comprises at least one coil at the distal end of navigation guidewire (40). When such a coil is positioned within an alternating electromagnetic field generated by field generators (24), the alternating magnetic field may generate electrical current in the coil, and this electrical current may be communicated along the electrical conduit(s) in navigation guidewire (40) and further to processor (12) via coupling unit (42). This phenomenon may enable IGS navigation system (10) to determine the location of the distal end of navigation guidewire (40) or other medical instrument (e.g., dilation instrument, surgical cutting instrument, etc.) within a three-dimensional space (i.e., within the head (H) of the patient (P), etc.). To accomplish this, processor (12) executes an algorithm to calculate location coordinates of the distal end of navigation guidewire (40) from the position related signals of the coil(s) in navigation guidewire (40). While the position sensor is located in guidewire (40) in this example, such a position sensor may be integrated into various other kinds of instruments, such as dilation catheters, guide catheters, guide rails, suction instruments, pointer instruments, registration probes, curettes, patient trackers, and other instruments, including those described in greater detail below.

Processor (12) uses software stored in a memory of processor (12) to calibrate and operate IGS navigation system (10). Such operation includes driving field generators (24), processing data from navigation guidewire (40), processing data from operating controls (14), and driving display screen (16). In some implementations, operation may also include monitoring and enforcement of one or more safety features or functions of IGS navigation system (10). Processor (12) is further operable to provide video in real time via display screen (16), showing the position of the distal end of navigation guidewire (40) in relation to a video camera image of the patient's head (H), a CT scan image of the patient's head (H), and/or a computer generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pat. No. 10,463,242, entitled "Guidewire Navigation for Sinuplasty," issued Nov. 5, 2019, the disclosure of which is incorporated by reference herein. In the event that the operator is also using an endoscope, the endoscopic image may also be provided on display screen (16).

The images provided through display screen (16) may help guide the operator in maneuvering and otherwise manipulating instruments within the patient's head (H) when such instruments incorporate navigation guidewire (40). It should also be understood that other components of a surgical instrument and other kinds of surgical instruments, as described below, may incorporate a sensor like the sensor of navigation guidewire (40).

Figure 2A:
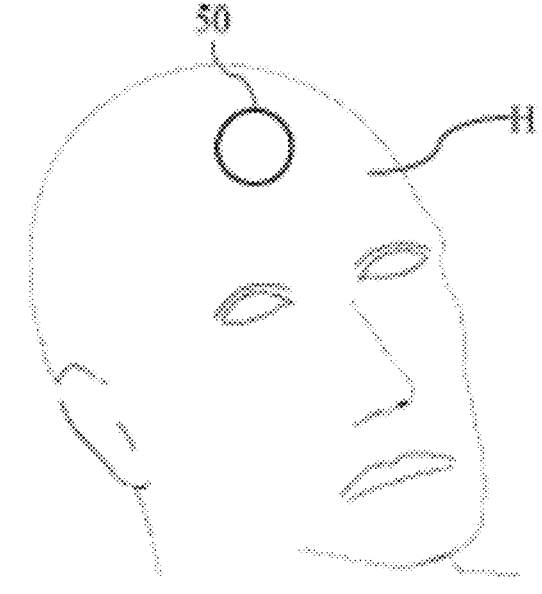
FIG. 2A depicts a schematic view of an exemplary patient tracker placed on the patient of FIG. 1.

In some implementations, the IGS navigation system (10) may include a patient tracking assembly (50) that may be placed on the head (H) of the patient, or another appropriate portion of the patient (P) as shown in FIG. 2A. By tracking the head (H) separately from the guidewire (40) but within the same coordinate system, the positions and orientations of the guidewire (40) and the head (H) may be determined relative to each other during a procedure. This may be advantageous where the head (H) is registered to determine its initial position within the coordinate system, but then later moves during the procedure. By tracking the head (H) independently, a rotation or other movement may be detected, and the initial registration may be updated to account for the new position of the head (H). In this manner, any image guided navigation features being used during the procedure, such as the display of CT image slices with overlaid markers indicating the position of the guidewire (40) within the head (H), may be automatically updated in response to such movements. Implementations of the patient tracking assembly (50) may be constructed and operable with the IGS navigation system (10) in accordance with any of the teachings of U.S. Pat. Pub. 2019/0183582, entitled "Mounted Patient Tracking Component for Surgical Navigation System," filed Dec. 14, 2017, the disclosure of which is incorporated by reference herein.

Figure 2B:
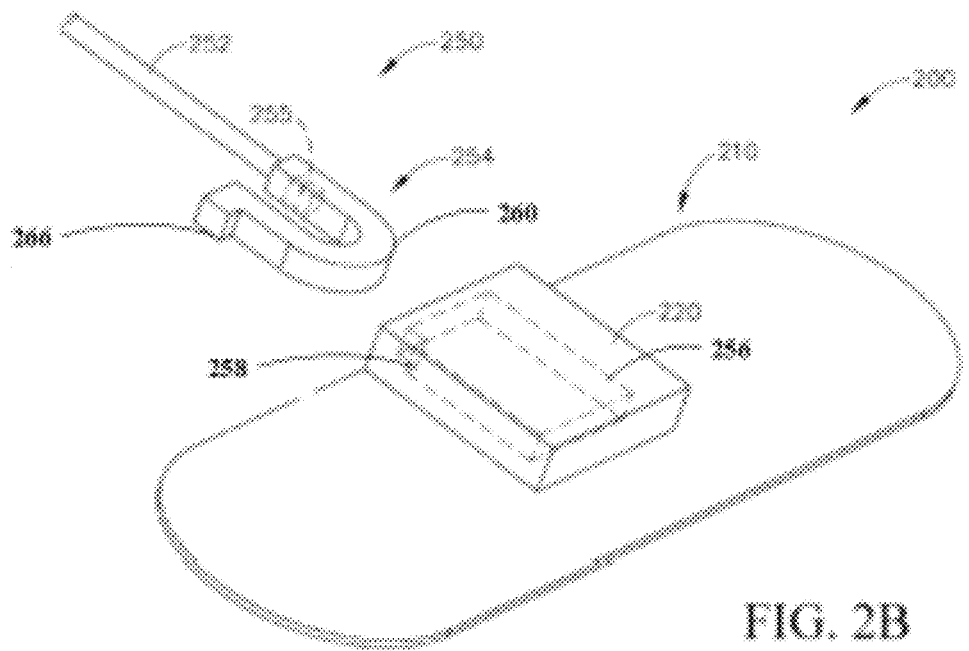
FIG. 2B depicts a perspective view of an exemplary patient tracker, such as that shown in FIG. 2A.

As one example of the patient tracking assembly (50), FIG. 2B shows a patient tracking assembly (200) that may be readily incorporated into the IGS navigation system (10). The patient tracking assembly (200) includes a disposable portion (210) and a reusable portion (250). The disposable portion (210) is configured to attach to the patient's head (H), or another suitable portion of patient (e.g., using a flexible adhesive pad), and includes a coupling block (220) that is configured to selectively couple with a coupling assembly (254) of the reusable portion (250) such that the reusable portion (250) is fixed relative to the head or another portion of patient (P) during exemplary use; while the reusable portion (250) is configured to communicate with the processor (12) in order to track the position of the head (H) of patient (P).

The reusable portion (250) includes a cable (252) extending proximally from the coupling assembly (254), and a sensor (255). The coupling assembly (254) is adapted to couple the reusable portion (250) with the disposable portion (210) during use. The coupling assembly (254) includes a U-shaped latch (260) with a locking member (266) that is an offset from the U-shaped latch (260). The U-shaped latch (260) is configured to be received in an inner chamber (256) of the coupling block (220). When the U-shaped latch (260) is inserted into the inner chamber (256), the locking member (266) interfaces with a locking inset (258) located in the inner chamber (256). When properly coupled with the disposable portion (210), the sensor (255) may be utilized with the processor (12) to determine the location of the tracked anatomy, such that the processor (12) may accurately display the location of the navigation guidewire (40) (or any other suitable instrument) relative to the anatomy of patient (P) during exemplary use. The cable (252) is configured to provide a conduit for communication between the sensor (255) and the processor (12) during exemplary use. Therefore, the cable (252) may directly connect such that sensor (255) is in wired communication with the processor (110) via the cable (252). Alternatively, the cable (252) may connect the sensor (255) with a wireless communication device that is in wireless communication with the processor (12), similar to how the coupling unit (42) establishes wireless communication between the navigation guidewire (40) and the processor (12).

II. Exemplary Visualization System for ENT Procedures

Figures 3, 4:
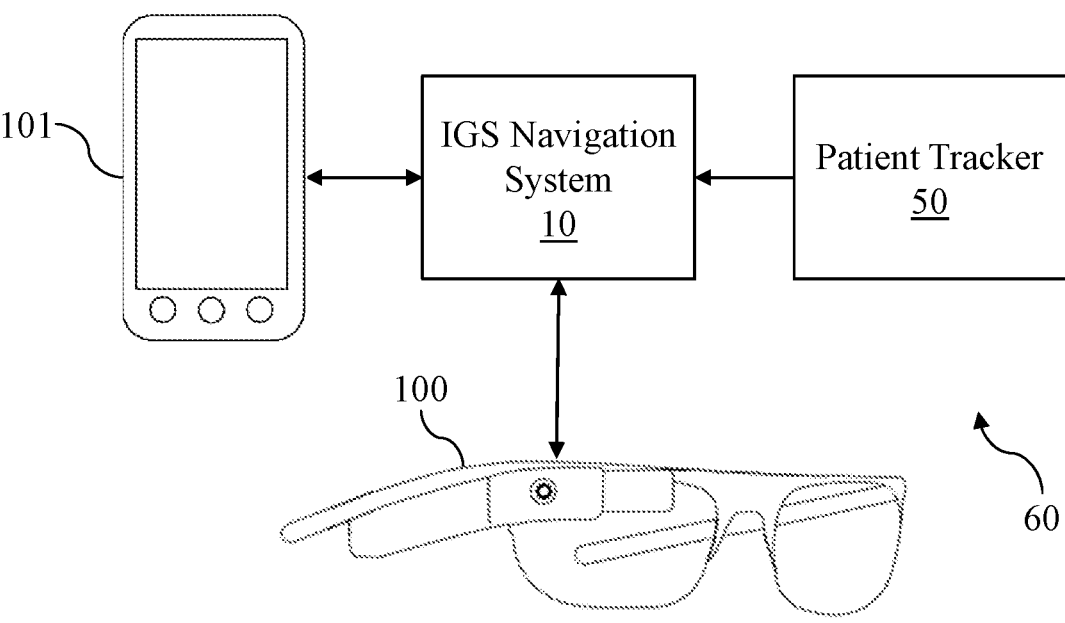
FIG. 3 depicts a schematic view of exemplary viewing devices usable with the surgery navigation system of FIG. 1.
FIG. 4 depicts a perspective view of one exemplary viewing device shown in FIG. 3.

FIG. 3 shows a visualization system (60) that may be implemented with the IGS navigation system (10) in order to provide additional information and image navigation views during a surgical procedure. In particular, the visualization system (60) may provide navigation views that display information in an augmented reality view that is overlaid upon images of the patient that are captured during a procedure in near real-time. This may advantageously reduce the frequency and need for a surgeon to view the display screen (16) or another display instead of viewing the patient during a procedure, and may also aid the surgeon in spatially orienting themselves between the physical world and the image navigation views provided by the IGS navigation system (10).

The visualization system (60) may be implemented with the IGS navigation system (10) by configuring one or more of a head mounted display ("HMD") (100), a handheld display ("HHD") (101), or another similar device to communicate with the IGS navigation system (10) during an image guided surgical procedure, as will be described in more detail below. FIG. 4 shows a perspective view of the HMD (100), which includes a frame (102) that may be worn on the face of a surgeon or other user involved with the image guided surgical procedure. A case (108) is shown mounted to the frame (102), but may also be worn or mounted elsewhere and coupled with devices mounted on the frame (102) via a wired or wireless connection to those devices. The case (108) includes a perspective sensor (110) that is operable to provide spatial information indicating the perspective, the location, or both of the HMD (100). The perspective sensor (110) may include one or more of a gyroscope, an accelerometer, or a position sensor (e.g., such as the sensor of the guidewire (40)), for example. Information from the perspective sensor (108) may be usable to determine one or more aspects of a visual perspective of a camera (106) that is mounted to the frame (102), which may include determining the orientation of an optical axis the camera (106) (e.g., rotational coordinates for one or more axes), the location of the camera (106) relative to the coordinate system of the IGS navigation system (10) (e.g., position coordinates for one more axes), or both, as will be described in more detail below.

The case (108) also includes a communication device (112), which may be a wired or wireless transceiver capable of communicating with the processor (12) or other devices, and a processor and memory (114) configured to process and store data and execute functions related to the function of the HMD (100). A power source (116) is also included, which may be a battery or a connection to an external power source, and which is configured to provide power to the processor and memory (114), communication device (112), camera (106), display (104), and other components of the HMD (100).

When worn, the frame (102) positions the camera (106), which is mounted to the frame (102) and/or the case (108), such that its optical axis is substantially parallel to an optical axis of the wearer's eyes when the wearer looks straight ahead. When used herein, the term "neutral optical axis" may refer to the optical axis of a wearer's eye, when the wearer of the HMD (100) looks substantially straight ahead (e.g., where the pupil of the eye is substantially centered both vertically and horizontally within the orbit or socket of the eye). In this manner, the camera (106) captures images that have a similar field of view as that of the wearer of the HMD (100). As an example, the camera (106) may capture images that include some or all of the field of view of the wearer's right eye, which the camera (106) is positioned most proximately to, when the wearer is looking straight ahead. The camera (106) may be capable of capturing images, video, and audio, which may be stored by the processor and memory (114), transmitted to the processor (12) via the communication device (112), or transmitted to and displayed or presented on another device, as will be apparent to those skilled in the art in light of this disclosure. Image data captured by the camera (106) may also be used for computer vision and other analysis which may include, for example, identifying objects or other visual characteristics of a captured image. Such analysis may be performed by the processor (114), the processor (12), or both, or may also be performed using various cloud computing or edge processing techniques, as will be apparent to those skilled in the art in light of this disclosure.

A display (104) is also mounted to the frame (102) and/or the case (108) and is positioned to be within the field of view of the wearer of the HMD (100). In some implementations, the display (104) is at least partially translucent if not transparent and is operable by the processor (114) to render images that appear to be overlaid upon the field of view of the wearer. As an example, the display (104) may display an image captured by the camera (106), which may block some or all of the wearer's field of view from the proximate eye, but would otherwise appear similar to the wearer's normal field of vision for that eye. As another example, image analysis may be performed on a captured image to identify objects of interest within that image (e.g., in the context of surgical navigation, a human face or another portion of human anatomy), and the display (104) may be operated to render a visual marker that appears, to the wearer, to be overlaid upon their direct view (e.g., viewed through the transparent portion of the display (104)) of the identified object. In some implementations of the above, optical markers or other fiducial markers may be placed on objects of interest in order to provide image data having objects that are easily identifiable due to their reflectivity, shape, or other visual characteristics, such that an optical marker placed on a human face may be identified rather than the human face itself.

As yet another example, the display (104) may be operated to render visual markings that overlay the wearer's direct view of their field of view based on other inputs instead of or in addition to image analysis or machine vision. This may include, for example, rendering visual markings based on information from the perspective sensor (110), the processor (12), the patient tracker (50) (e.g., through communication with the processor (12)), and other devices. This could include rendering a visual marking providing information associated with the rotational perspective of the HMD (100) (e.g., based on a gyroscopic feature of the perspective sensor (100)). As another example, this could include rendering a visual marking that overlays a surgical instrument (e.g., the guidewire (40)), based upon tracking information associated with the surgical instrument and the HMD (100). In other words, when the processor (12) is able to track and determine the relative positions of the surgical instrument and the HMD (100), and the orientation of the HMD (100) may be determined (e.g., using the perspective sensor (110)), the position and scale of the tracked objects relative to each other may be determined and produced as rendered markings via the display (104).

As will be apparent to those skilled in the art in light of this disclosure, some or all of the above features may also be performed with other displays beyond the display (104). For example, in some implementations, a separate display (e.g., the display screen (16) or a wall mounted display that is visible to the entire room) may be configured to receive and display images captured from the camera (106) and any markings, renderings, or other overlay data that may be added. In such an implementation, the display (104) may render only overlay images, while the separate display may render a combination of an image captured by the camera (106) and any corresponding overlay images. This may allow other participants in the procedure to view the additional navigation views in addition to the wearer of the HMD (100). In some such implementations, the HMD (100) may not include the display (104), and combinations of captured images and rendered overlays may be viewable on the display screen (16) or another display positioned near the patient.

The HHD (101) may share some or all of the capabilities of the HMD (100), and may be, for example, a smartphone, a tablet, a proprietary device, or other handheld computing devices having capabilities such as processing and storing data, executing functions, sending and receiving data, capturing images, providing spatial information (e.g., orientation, location, or both). The display of the HHD (101) may commonly be a LED or LCD display, and so may not be capable of overlaying rendered markings onto a transparent surface through which objects are viewed directly, such as the display (104) might. In some implementations, the HMD (100) or HHD (101) may be modified to include additional capabilities. For example, some implementations of the HMD (100) may not include the capability to self-position relative to the coordinate system of the IGS navigation system (10). In such cases, a sensor may be mounted (e.g., externally or internally) on the HMD (100) that allows it to interact with and be tracked by the IGS navigation system (10), similar to the guidewire (40) and the patient tracking assembly (50). Thus, the capabilities of the perspective sensor (110) may include both those present in the HMD (100) by default, as well as those that may be later added, whether they are within the case (108) or externally mounted on the HMD (100).

In some implementations, information indicating the orientation and location of the HMD (100) may be available from multiple sources. As one example, the perspective sensor (110) may include a gyroscopic feature capable of determining rotational orientation, may include or incorporate a tri-axis sensor capable of being tracked by the IGS navigation system (10) to determine rotational orientation, and may be configured to identify optical fiducials present within images captured by the camera (106). In such examples, the processing components (e.g., the processor (114), the processor (12), or other processors) may be configured to determine orientation or location in various ways by balancing performance and accuracy, as will be apparent to those skilled in the art in light of this disclosure. For example, some implementations may determine orientation or location based only on gyroscopic information from the HMD (100) itself or tracking information from the IGS navigation system (10) to emphasize performance, while other implementations may use a combination of gyroscopic, magnetic tracking, and image analysis information with a goal of achieving a higher accuracy at the potential cost of some performance (e.g., the delay, if any, between the orientation or location of the HMD (100) changing and a determination of the new orientation or location being completed).

The visualization system (60) allows for additional inputs and information to be gathered and used during surgical navigation in order to provide additional navigation views and other feedback to users of the HMD (100) or the HHD (101), or viewers of other displays that are configured to display images from the camera (106) and any corresponding overlay renderings. In the absence of the visualization system (60), there is a breadth of useful information available to the IGS navigation system (10) that is largely confined to being used or displayed in the context of pre-operative images (e.g., 3-D patient models produced from pre-operative imaging, CT, MRI, or ultrasound image sets).

As an example, the IGS navigation system (10) may allow a surgeon to view a set of CT images for a patient prior to a procedure and plot out a surgical plan or surgical path that the surgeon will navigate one or more surgical instruments along during the procedure. During the procedure, the surgical path may then be overlaid on the CT image set and displayed via the display screen (16), allowing the surgeon to switch between a limited number of views (e.g., axial, coronal, sagittal) and slices as may be desired. As another example, during a procedure, a surgical instrument (e.g., the guidewire (40)) may also be tracked and similarly displayed on the CT image set. When displayed together, a surgeon may find it beneficial to view CT images that show the tracked position of the surgical instrument and the planned surgical path in relation to each other.

While useful, the above features can distract the surgeon's attention from the patient, as they may need to look away from the patient to view a nearby display device. It can also be disorienting when switching between the axial, coronal, and sagittal views, as the surgeon's actual location relative to the patient has not changed. For example, a surgeon may be viewing an axial plane CT image of the patient head and, when returning their view to the patient, may be observing a sagittal plane of the patient's head. In order to make use of the information displayed on the CT image, such as the location and orientation of the surgical instrument, the surgical path, and nearby anatomical cavities and structures, the surgeon must first mentally transform or relate their spatial understanding of the axial plane to the sagittal plane in order to know which direction to navigate the surgical instrument. This process can be mentally taxing, may consume valuable time during a procedure, and may also lead to erroneous navigation of the surgical instrument.

To address this, the visualization system (60) provides a framework for relating the coordinate system and associated information to the physical world perceived by the wearer of the HMD (100). Such associated information may include, for example, CT images, configured surgical paths, real time surgical instrument tracking, real time patient tracking, configured points of interest indicating areas that should be investigated or avoided, and other similar information that may be correlated to a coordinate system for IGS navigation, which may be collectively referred to herein as correlated datasets.

Once related, these correlated datasets can then be displayed via the display (104) so that they are available when directly looking at the patient instead of only being displayed on the display screen (16) or another nearby display. In addition to reducing the need to refer to external displays, such an implementation allows the wearer of the HMD (100) to browse or navigate the correlated datasets by changing their perspective relative to the patient, instead of using a mouse or keyboard to step through image slices, switch between viewable planes, or rotate 3-D models. For example, in the case of a tracked surgical instrument location and surgical path, the surgeon may be able to view a rendered overlay of the instrument location and surgical path within the patient's head from different perspectives by moving and observing from different angles, rather than being confined to stepping through CT image slices and between CT image planes using a mouse or keyboard interface.

Figure 5:
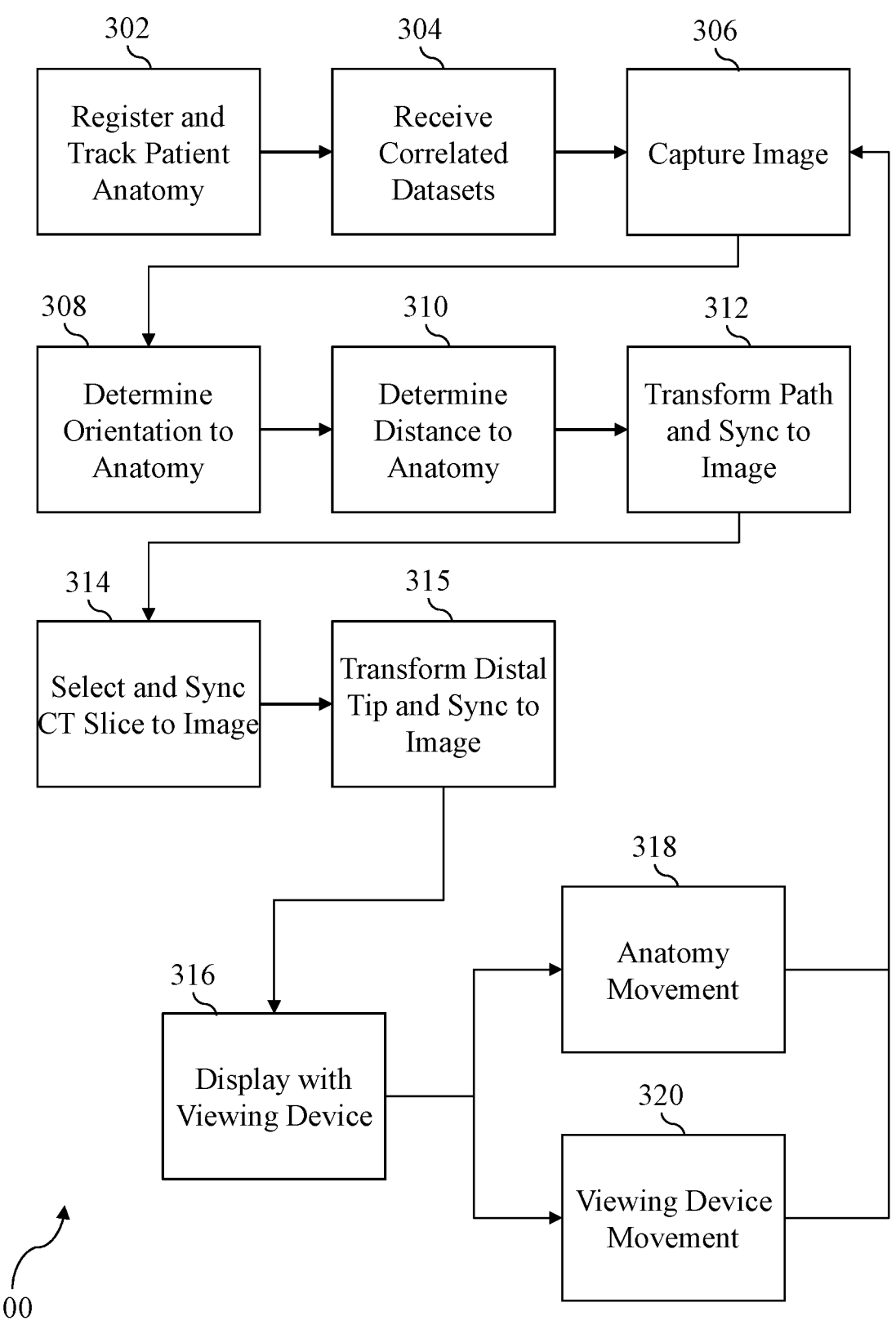
FIG. 5 depicts a flowchart of an exemplary set of steps that may be performed with the surgery navigation system of FIG. 1 to provide visualization for ENT procedures.

As an exemplary implementation of the above, FIG. 5 shows a set of steps (300) that may be performed with the visualization system (60) to render and display correlated datasets via the HMD (100) or another viewing device, while FIGS. 6A-6C and FIGS. 7A-7C show exemplary interfaces that may be displayed or viewed with the visualization system (60). After positioning a patient for a procedure, the patient may be registered (block 302) and, in implementations including the patient tracking assembly (50), tracked within the IGS navigation coordinate system. Registration of the patient may include using a registration probe or other device to provide the coordinate system with a plurality of locations that correspond to patient anatomy, may include placing, calibrating, and using the patient tracking assembly (50), or both, or may include other registration techniques. Registration (block 302) may also include registering and tracking other devices and instruments, such as the guidewire (40) and other trackable surgical instruments. Registration (block 302) may also include registering and tracking the HMD (100), where it is capable of being positionally tracked by the IGS navigation system (10).

The IGS navigation system (10) may also receive (block 304) one or more correlated datasets that are associated with the patient and procedure, which may include pre-operative images of the patient anatomy (e.g., CT, MRI, and ultrasound image sets), pre-configured surgical plans and surgical paths, and other pre-configured or pre-operatively captured or generated datasets that may be associated with the IGS navigation coordinate system. The received (block 304) correlated datasets may also include data that is captured in real-time during the procedure and then associated with the coordinate system, such as position tracking data indicating the location of the guidewire (40) and other tracked surgical instruments, and position tracking data indicating the location of the HMD (100).

When the HMD (100) or another device (e.g., the HHD (102)) is in use with the visualization system (60), images may be captured (block 306) by the camera (106), as has been described. In some implementations, images will be captured (block 306) constantly based upon a configured framerate of the camera (106), such that each subsequent image may change slightly from the previous image based upon movements of the wearer of the HMD (100). Captured (block 306) images may be stored by the processor and memory (114) and may be transmitted to the processor (12) or another device.

As images are captured (block 306), the visualization system (60) may repeatedly determine (block 308) the orientation of the HMD (100) relative to the anatomy and repeatedly determine (block 310) the distance of the HMD (100) relative to the anatomy. These determinations (block 308, block 310) may be made continuously and independently, or may be made for each captured (block 306) image one a one-to-one basis (e.g., where the camera (106) captures thirty images or frames per second, the visualization system (60) would determine orientation (block 308) and distance (block 310) thirty times per second, once for each image) or some other correspondence (e.g., the visualization system may be configured to determine orientation (block 308) and distance (block 310) once for every three captured (block 306) images), as will be apparent to those skilled in the art in light of this disclosure.

The orientation (308) and distance (310) may be determined in varying ways, as has already been described. For example, in some implementations, each of the HMD (100) and the patient head (H) may be positionally and orientationally tracked by the IGS navigation system (10) and the distance and orientation may be determined using the IGS navigation coordinate system. In some implementations, the orientation and/or distance may be determined using the perspective sensor (110) of the HMD (100).

Figure 6A:
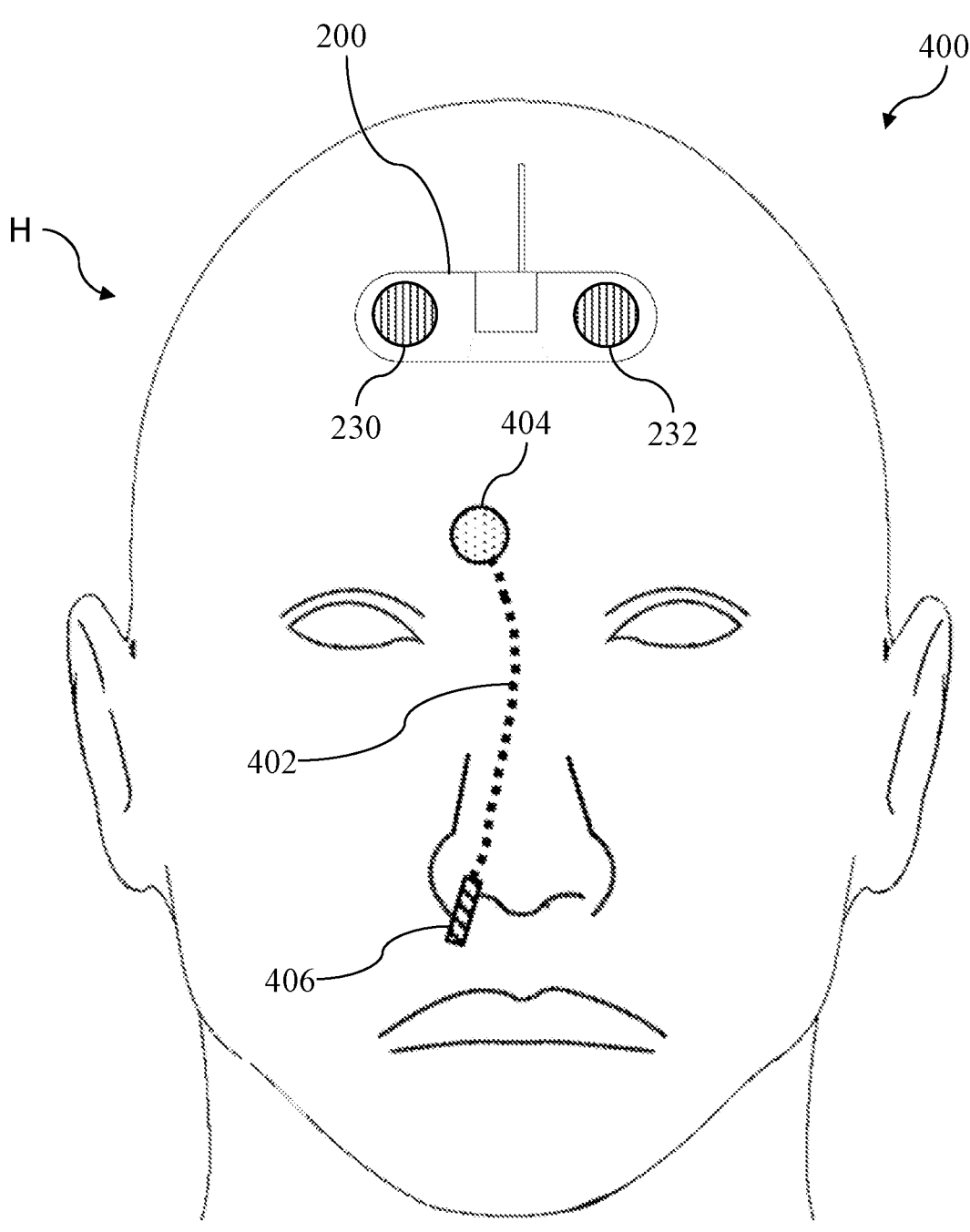
FIG. 6A depicts an exemplary interface showing a front view of a patient face that may be provided during visualization for ENT procedures.

In some implementations, the orientation and/or distance may be determined using image analysis of a captured (block 306) image to identify a particular object (e.g., an optical fiducial) or patient anatomy (e.g., an eye). For example, particularly in the case of an optical fiducial having a predictable size, shape, and other characteristics, image analysis of an image containing the optical fiducial can indicate the distance and perspective from which the optical fiducial is viewed. With reference to FIG. 6A, the patient tracking assembly (200) can be seen placed on the head (H) of a patient. One or more optical fiducials (230, 232) may be placed on the patient tracking assembly (200) or elsewhere, as may be desirable.

The appearance of the optical fiducial (230) in an image provides an indication of the perspective from which the image was captured (e.g., the optical fiducial (230) may appear as a circle when viewed as shown in FIG. 6A, but may appear as an oval as a viewer moves to the left or right) as well as the distance (e.g., the optical fiducial might have a diameter of 2 cm. Where the optical fiducial (230) has an asymmetrical shape of sufficient complexity, or where the surface of the optical fiducial (230) has a pattern or other visible characteristic of sufficient complexity, a single fiducial may provide enough information to fully determine orientation and distance.

Additionally, where several optical fiducials (230, 232) are used, such as is shown in FIG. 6A, the apparent positions of each fiducial relative to the others may be used as an indication of orientation. As such, it may be advantageous to place two or more optical fiducials on the tracking assembly (200) or the head (H). In some implementations, one or more fiducials may be integrated onto the surface of the tracking assembly (200) at the time of manufacture, which may advantageously indicate a static and known positioning and distance from each other which may be used to aid in subsequent fiducial based orientation and distance determinations.

As has been described, implementations may vary in the particular approach that is taken for determining the orientation (block 308) and the distance (block 310), and while some implementations may rely entirely on tracking each object of interest within the IGS navigation coordinate system, others may combine such tracking with image analysis of optical fiducials or other techniques in order to improve accuracy, performance, or other characteristics of the results. As such, it should be understood that various combinations of the disclosed methods and others exist and will provide varying advantages for determining the orientation (block 308) and the distance (block 310), and such combinations will be apparent to those skilled in the art based on this disclosure.

Once determined, the distance and orientation relative to the viewed anatomy can then be used to transform a correlated dataset so that it may be displayed via the display (104) as a rendered overlay of the viewed anatomy, or displayed via another device as a rendered overlay of a captured image. Correlated dataset transformations may include, for example, transforming (block 312) a surgical path to match the scale and perspective of the captured (block 306) image, transforming (block 314) a CT image or other image type to match the scale and perspective of the captured (block 306) image, transforming (block 315) the tracked location of a surgical tool distal tip to match the scale and perspective of the captured (block 306) image, and other transformations. While they are discussed within the context of FIG. 5, it should be understood that a surgical path, CT image, and tracked surgical tool are not required to be present within the received (block 304) correlated datasets.

Figure 8:
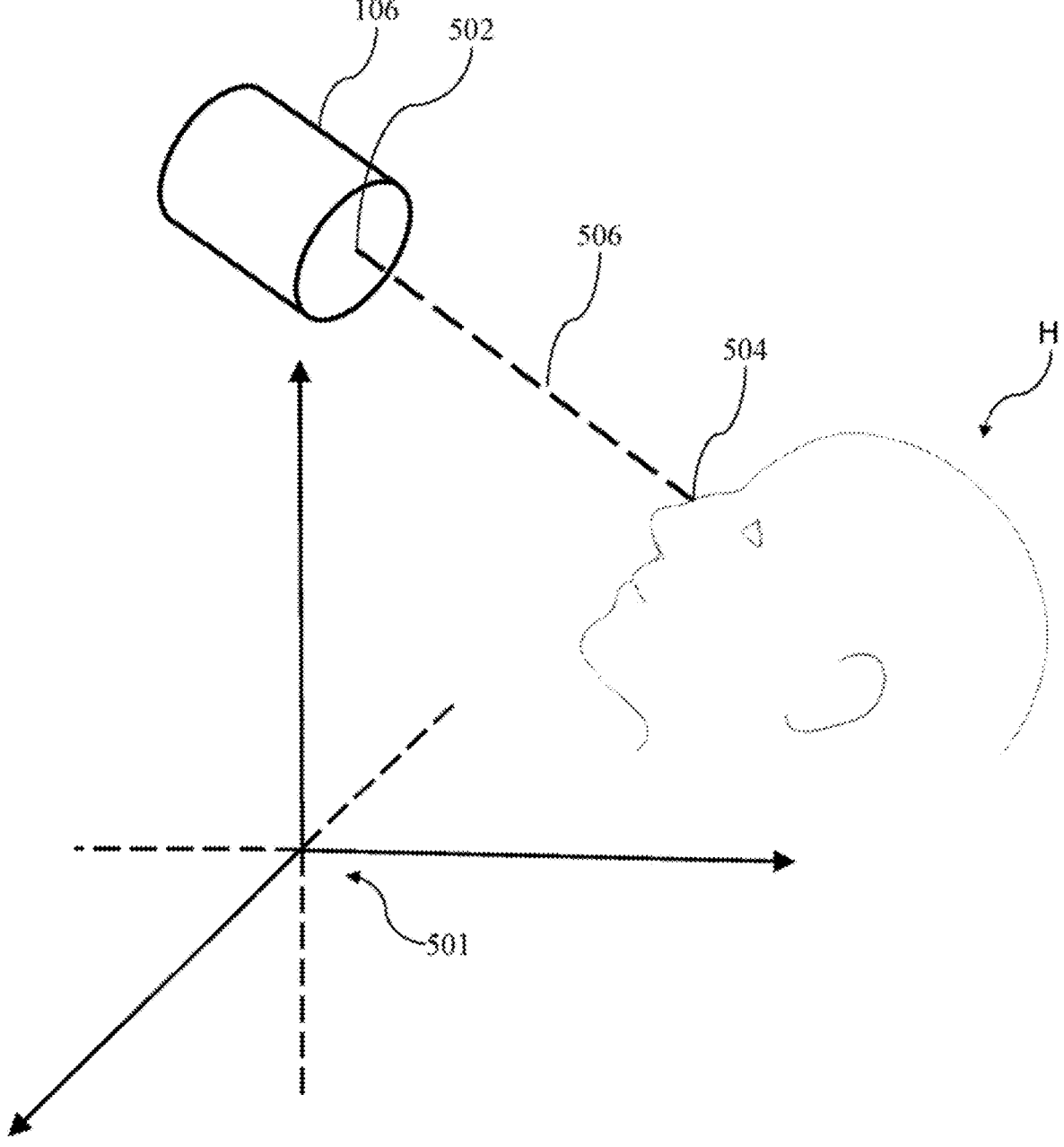
FIG. 8 depicts a schematic diagram that illustrates the relative locations and orientations of a camera and a patient's head within a three-dimensional coordinate system.

Transformation of correlated datasets will vary depending upon the particular data represented in a correlated dataset. For example, with reference to FIG. 8, where the system is configured to overlay some or all of a CT image slice on a patient's head (H), the distance (506) between a perspective point (502) (e.g., the lens of the camera (106)) and a viewed point (504) (e.g., the first point, voxel, or other object within the coordinate system intersected by the optical axis of the camera (106)) may be used to determine and apply a scaling factor to transform and control the scale at which the CT image slice is displayed via the display (104). As the wearer of the HMD (100) moves toward the head (H), the distance (506) will reduce and the scale of the displayed CT image slice will increase. Similarly, movement away from the head (H) will increase the distance (506) and reduce the scale of the displayed CT image slice. In this manner, the scaling factor can be configured to provide, based on the distance (506), an appropriately sized rendering of the CT image that corresponds to the perceived size of the head (H) at that distance.

Continuing the above example, the position of the perspective point (502) relative to the viewed point (504), within a three dimensional coordinate system (501), may be used to determine an appropriate CT image slice to render, and may be used to transform an appropriate CT image slice so that it may be overlaid on the head (H). As an example, in some implementations a CT image slice of the head (H) may be selected and rendered as an overlay depending upon the perspective from which the head (H) is viewed, such that a perspective above the head (H) might show an axial view, a perspective from in front of the head (H) might show a coronal view, and a perspective from the side of the head might show a sagittal view, and views may be switched automatically as the wearer of the HMD (100) moves between perspectives.

As another example, in some implementations a CT image slice may be transformed to create a new image having an appearance of that of the two-dimensional input image as if it were fixed in place and viewed from a different perspective (e.g., a two-dimensional image perspective transformation). In this manner, a two-dimensional CT image slice displayed on the head (H) might be perspective transformed as the wearer of the HMD (100) moves between perspectives.

As yet another transformation example, in the case of a correlated dataset containing a surgical path the coordinates of the surgical path may be rendered and overlaid on the head (H) as a set of points, a line, or a dotted line. The distance (506) may be used to transform the scale of the surgical path so that, when overlaid upon the head (H), each coordinate of the surgical path is appropriately positioned relative to the head (H). The position of the perspective point (502) relative to the viewed point (504) within the coordinate system (501) may be used to transform the surgical path as the wearer of the (HMD) moves between perspectives. Such a transformation may be performed as a perspective transformation, as described above, or may be performed using other three dimensional rotational and depth transformations, as will be apparent to those skilled in the art based on the disclosure herein.

After each correlated dataset is transformed (e.g., scaled, perspective transformed, or otherwise), they may be rendered or displayed (block 316) on one or more viewing devices, which may include displaying rendered markers as overlays via the display (104), displaying rendered markers as overlays on a captured image via the HHD (101) or another display, or both. For a user wearing the HMD (100), the rendered markers may appear to overlay objects within their field of view (e.g., the patient's head or other anatomy) that are viewed through the transparent display (104). For users of the HHD (101) or viewers of a wall mounted display or other device, a captured image may be displayed with the rendered markings overlaid thereon. As has been described, the steps of capturing images, determining perspective, and transforming correlated datasets may be repeated continuously as images are captured so that users may move and look around a procedure area as normal while receiving continuous updates of overlaid information.

For example, where either a movement of the viewed anatomy occurs (block 318) or a movement of the HMD (100), HHD (101), or other viewing device occurs (block 320), the next captured (block 306) image will be received, and the orientation (block 308) and distance (block 310) will be redetermined. The newly determined orientation and distance will then be used for one or more transformations, and the newly produced overlays will account for any movements or changes that have occurred since the prior image.

Figure 6B:
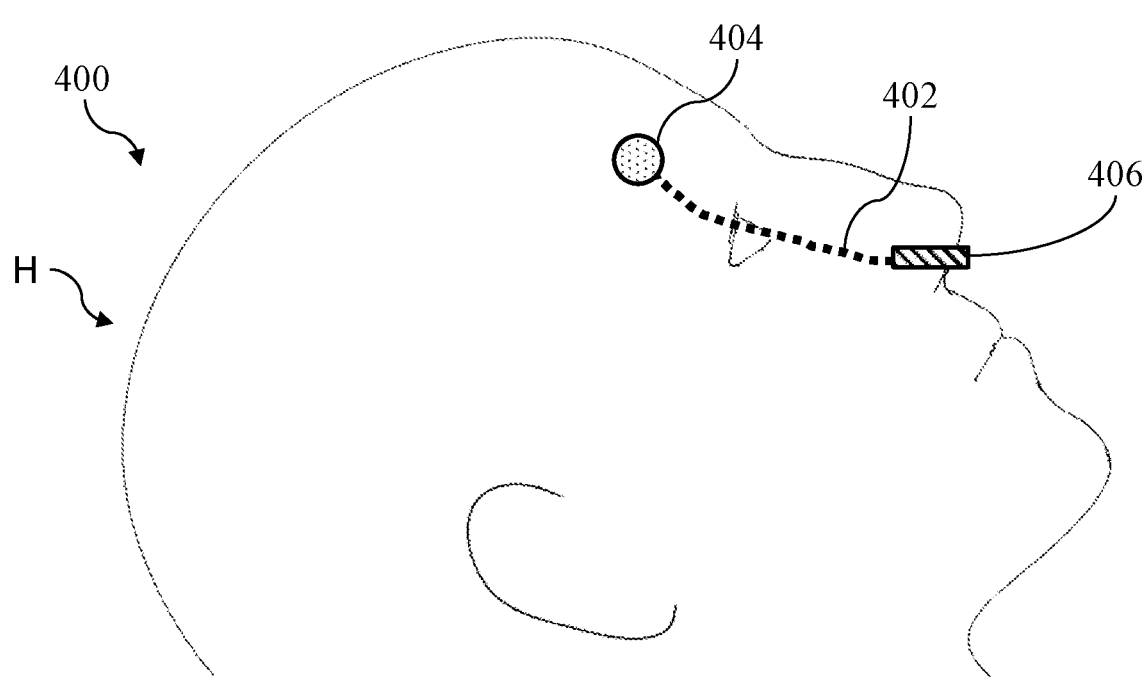
FIG. 6B depicts an exemplary interface showing a side view of a patient face that may be provided during visualization for ENT procedures.
Figure 6C:
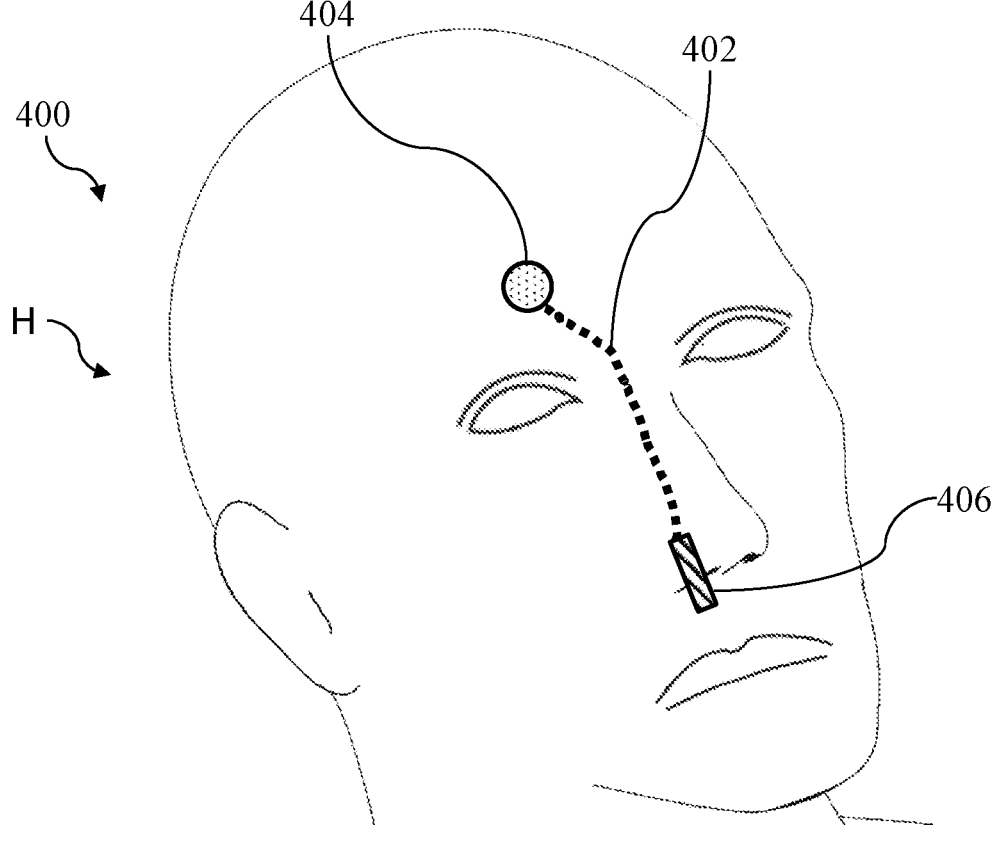
FIG. 6C depicts an exemplary interface showing a perspective view of a patient face that may be provided during visualization for ENT procedures.

FIGS. 6A-6C show an example of an interface (400) that includes a rendered and transformed surgical path, such as may be displayed via the display (104) and overlaid upon a directly viewed patient's head (H), or such as may be overlaid upon a captured image of the head (H) and displayed. In FIG. 6A, the head (H) is viewed from the front (e.g., a view of the coronal plane), and rendered markers have been overlaid via the display (104) or directly onto a captured image. The rendered markers include a surgical path (402) indicating the path that a surgical tool should follow, a target marker (404) indicating a destination or portion of anatomy involved in the procedure, and a tool marker (406) indicating the current location of a tracked surgical instrument. The scale of the markers has been determined based upon the determined distance (310), such that the surgical path (402) accurately overlays the patient's head (H) and appears as it would were it to be viewed directly on a coronal plane CT image slice rather than as an overlay rendered via the display (104) or another device. The positions and orientations of the markers have also been determined based upon the determined orientation (308).

FIG. 6B shows the head (H) viewed from the side (e.g., a view of the sagittal plane). Each marker has been rendered in a new position and orientation based upon the change in perspective. For example, in FIG. 6A the surgical path (402) is seen to traverse along the coronal plane of the head (H). The coronal plane is not visible in FIG. 6B, and the surgical path (402) can instead be seen traversing along the sagittal plane. Similarly, the position and orientation of the target marker (404) and tool marker (406) are each changed from FIG. 6A, and the depth at they are positioned within the head (H) can be determined. FIG. 6C shows the head (H) viewed from a third perspective, such as might be viewed when a viewer moves between the view of FIG. 6A and the view of FIG. 6B. As the viewer moves between the views of FIGS. 6A and 6B, or to other perspectives from which the head (H)

may be viewed, each of the markers may be updated and newly rendered to provide additional information and context without being limited to only those perspectives offered by a CT image set, and without needing to look away from the head (H) to the display screen (16) or another display, which may be distracting and disorienting as has been described.

Figure 7A:
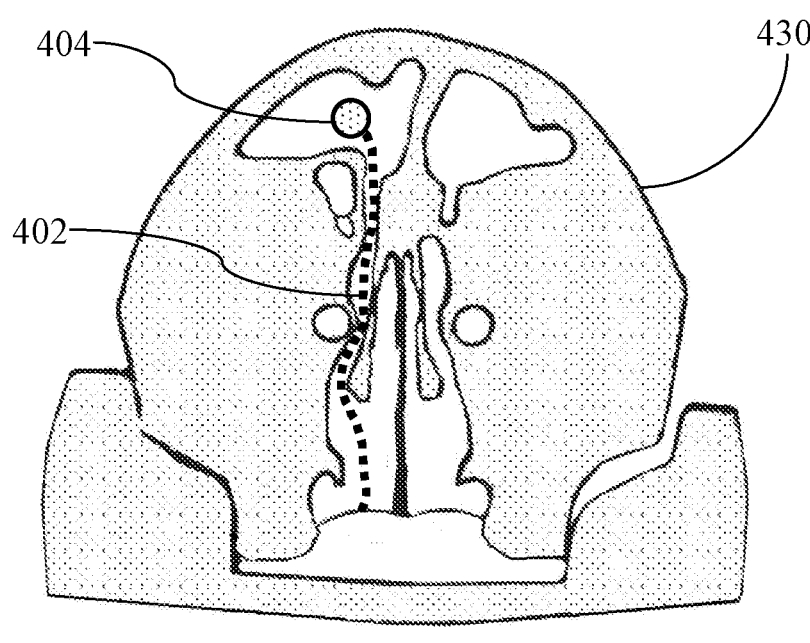
FIG. 7A depicts an exemplary computed tomography (CT) image usable with the surgery navigation system of FIG. 1.
Figure 7B:
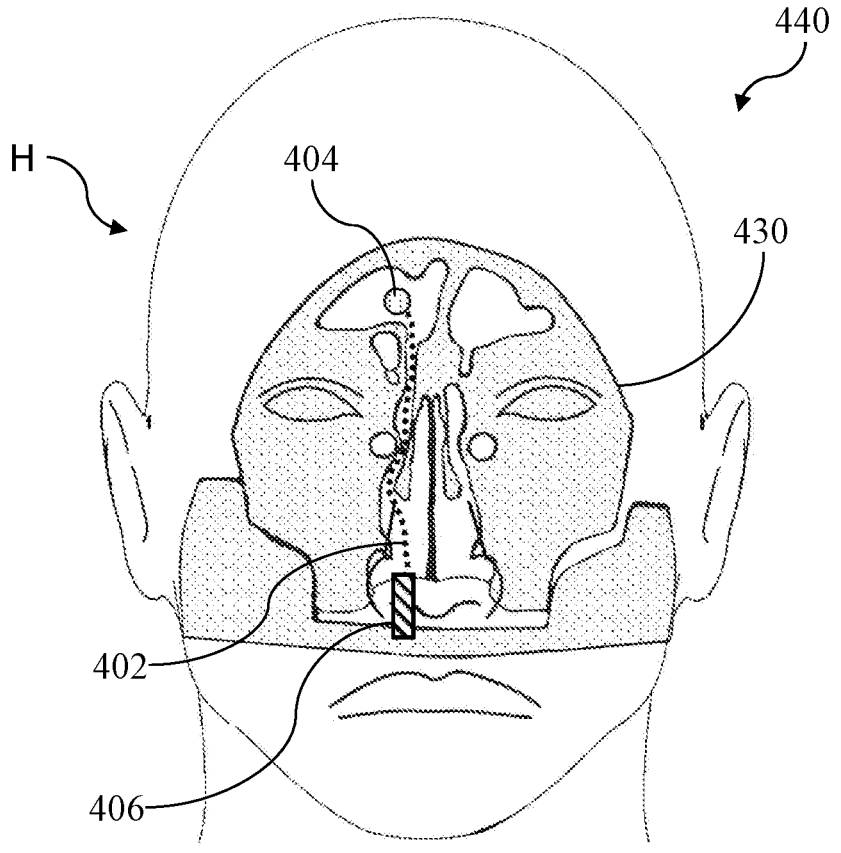
FIG. 7B depicts an exemplary interface showing a front view of a patient face with a CT image overlaid that may be provided during visualization for ENT procedures.
Figure 7C:
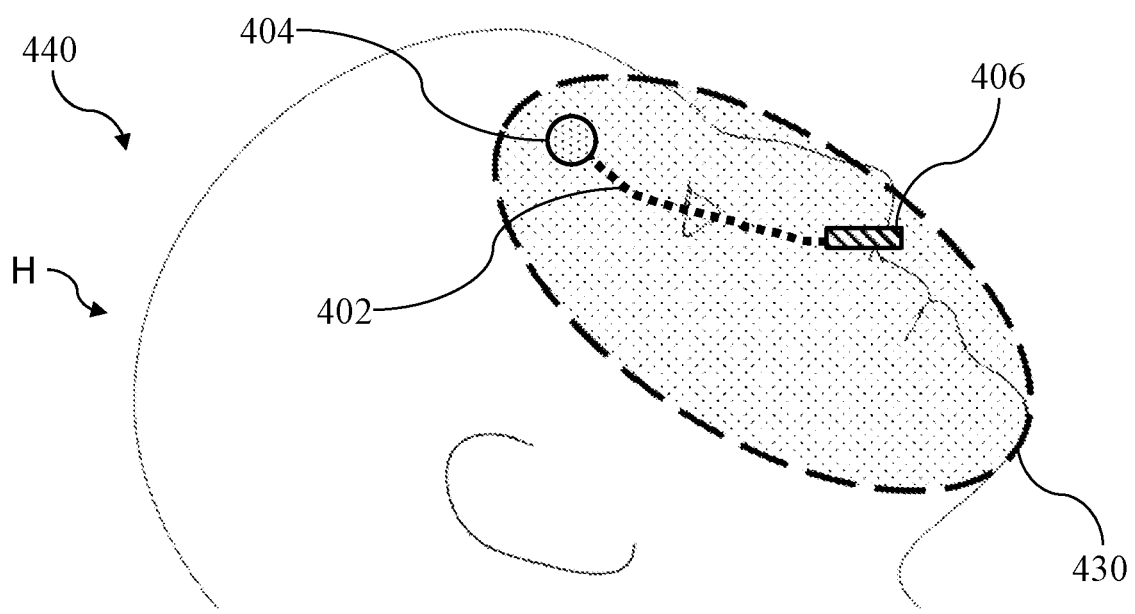
FIG. 7C depicts an exemplary interface showing a side view of a patient face with a CT image overlaid with the that may be provided during visualization for ENT procedures.
Figure 7D:
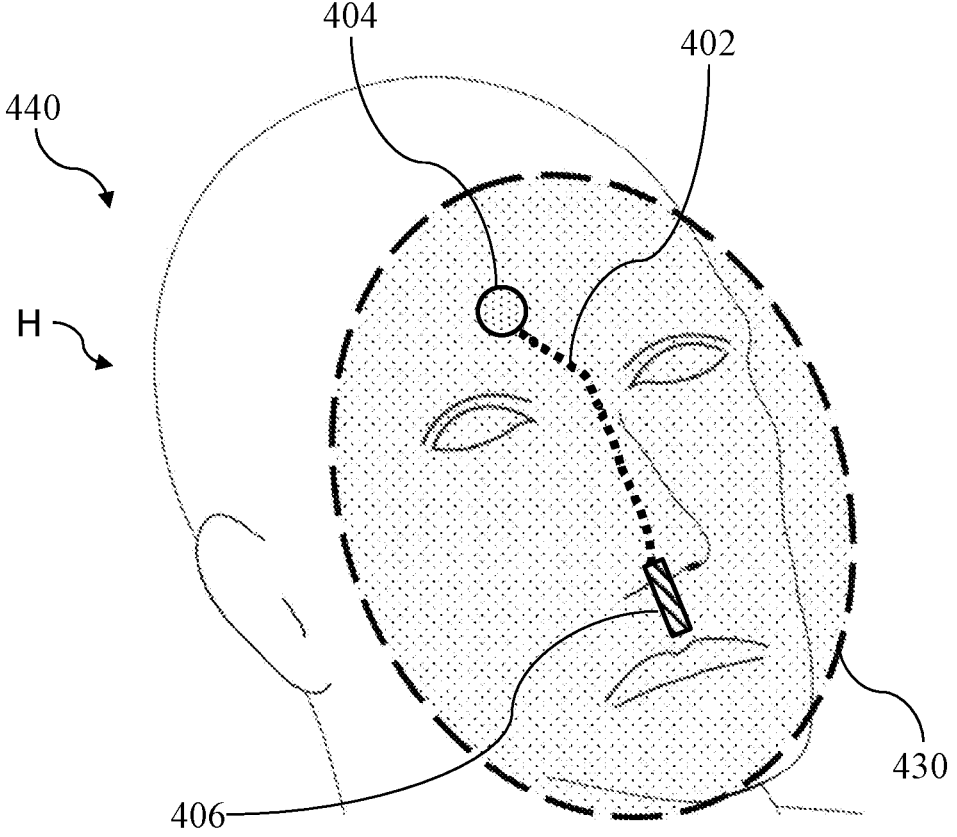
FIG. 7D depicts an exemplary interface showing a perspective view of a patient face with a CT image overlaid that may be provided during visualization for ENT procedures.

As another example of an interface that may be provided by the visualization system (60), FIG. 7A shows an image (430) selected from a CT image set, and FIGS. 7B-7D show an example of an interface (440) that includes a rendered overlay of the image (430) and the surgical path (402), such as may be displayed via the display (104) and overlaid upon a directly viewed patient's head (H), or such as may be overlaid upon a captured image of the head (H) and displayed. The image (430), the surgical path (402), and the target marker (404) may be received (304) as correlated datasets prior the procedure.

In FIG. 7B, the head (H) is viewed from the same perspective as that of FIG. 6A. The image (430) is also overlaid upon the head (H) after having been transformed so that the scale of the image (430) corresponds to the perceived size of the head (H) (e.g., as opposed to being too large such that the image (430) extends beyond the head (H)). The tool marker (406), surgical path (402), and target marker (404) may also be overlaid and visible with the CT image (430), and each may be rendered at varying degrees of transparency to either completely obfuscate direct viewing of the head (H) through the renderings, or to allow some degree of transparency. While varying implementations of the visualization system (60) may provide interfaces such as shown in FIGS. 6A-6C or FIGS. 7B-7D, some implementations may provide both, and may, for example, allow certain layers to be enabled or disabled as desirable. For example, this may include enabling or disabling the overlay of the image (430) over the head (H) as may be desired.

FIGS. 7C and 7D each show the head (H) from different perspectives, matching those shown in FIGS. 6B and 6C. The image (430) is simulated as a shaded area, and the other rendered markings are each transformed to account for the altered perspective. As has been described, FIG. 7B may show a substantially unaltered CT image of the coronal plane as the image (430), while FIG. 7C may show a substantially unaltered CT image of the sagittal plane as the image (430). In some implementations, FIG. 7D may show a transformed CT image from the coronal or sagittal plane, depending upon whether the viewer's perspective is closer to the coronal plane or the sagittal plane.

It should be understood that the interfaces of FIGS. 6A-7C are representative of interfaces that may be displayed when correlated datasets are rendered and overlaid on objects that are visible through the transparent portions of the display (104). For example, with reference to FIG. 6A, the head (H) is not rendered via the display (104) but is a visible part of the augmented reality interface because it is being viewed through the transparent portion of the display (104). The interfaces of FIGS. 6A-7C are also representative of interfaces that may be displayed when correlated datasets are rendered and overlaid on images captured via the camera (106), such as may be displayed via the display screen (16), or may be displayed via the HHD (101). With such interfaces, the head (H) would also be rendered on the display based on the captured image.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A system for ENT visualization comprising: (a) an image guided surgery ("IGS") navigation system operable to: (i) maintain a coordinate system corresponding to a tracked area, (ii) track one or more position sensors with the coordinate system, and (iii) register the location of a patient anatomy with the coordinate system; (b) a head mounted display ("HMD") comprising a wearable frame and a display, wherein the display is positioned on the wearable frame to be intersected by a neutral optical axis of the wearer; (c) a sensor operable to produce a set of perspective data indicating the perspective of the HMD relative to the patient anatomy; and (d) a processor; wherein the processor is configured to: (i) receive one or more correlated datasets, wherein each of the one or more correlated datasets comprise data associated with the coordinate system, (ii) while the patient anatomy is viewed from a present perspective, determine an orientation of the neutral optical axis relative to a viewed point on the patient anatomy based on the set of perspective data, (iii) determine a distance between an origin of the neutral optical axis and the viewed point based on the set of perspective data, (iv) transform the one or more correlated datasets based on the orientation and the distance to produce an overlay image that corresponds to the patient anatomy at the present perspective, and (v) render the overlay image via the display.

EXAMPLE 2

The system of example 1, wherein the one or more correlated datasets comprise: (i) a surgical path indicating a planned route of a surgical instrument within the patient anatomy, and (ii) a distal tip location indicating the current location of a distal tip associated with a position sensor of the one or more position sensors.

EXAMPLE 3

The system of example 2, wherein the one or more correlated datasets further comprise an image slice selected from a set of preoperative images of the patient anatomy.

EXAMPLE 4

The system of any one or more of examples 1 through 2, further comprising a patient tracking assembly positioned on the patient anatomy, wherein: (i) the patient tracking assembly comprises a position sensor of the one or more position sensors, and (ii) the IGS navigation system is configured to update the location of the patient anatomy with the coordinate system based on movements of the position sensor.

EXAMPLE 5

The system of example 4, wherein the sensor is mounted on the HMD and is one of the one or more position sensors, and wherein the processor is further configured to, when determining the orientation of the neutral optical axis relative to the viewed point: (i) determine an orientation of the neutral optical axis based on the coordinate system, (ii) determine an orientation of the patient anatomy based on the coordinate system, and (iii) correlate the orientation of the neutral optical axis and the orientation of the patient anatomy based on the coordinate system.

EXAMPLE 6

The system of any one or more of examples 4 through 5, wherein the sensor is mounted on the HMD and is one of the one or more position sensors, and wherein the processor is further configured to, when determining the distance between the origin and the viewed point: (i) determine a location of the origin based on the coordinate system, (ii) determine a location of the patient anatomy based on the coordinate system, and (iii) determine the distance between the location of the origin and the location of the patient anatomy based on the coordinate system.

EXAMPLE 7

The system of any one or more of examples 1 through 6, wherein the processor is further configured to, when transforming the one or more correlated datasets: (i) determine a scaling factor based on the distance between the origin and the viewed point, (ii) determine a perspective transform based on the orientation of the neutral optical axis relative to the viewed point, and (iii) produce the overlay image comprising a scale determined by the scaling factor and a perspective determined by the perspective transformation.

EXAMPLE 8

The system of example 7, wherein the display comprises a transparent screen, and wherein the processor is further configured to render the overlay image on the transparent screen such that the overlay image appears on a directly viewed portion of the patient anatomy.

EXAMPLE 9

The system of any one or more of examples 1 through 8, wherein the processor is further configured to: (i) repeatedly redetermine the distance and the orientation, and (ii) update and render the overlay image via the display as the distance and orientation change.

EXAMPLE 10

The system of any one or more of examples 1 through 9, wherein the sensor comprises a camera positioned on the wearable frame and having an optical axis that is parallel to and statically offset from the neutral optical axis, and wherein the processor is further configured to, when determining the orientation and the distance: (i) store an object dataset that indicates one or more visible characteristics of an object and indicates a relationship between the object and the viewed point within the coordinate system, (ii) receive an image from the camera that contains the object, and (iii) determine the orientation and the distance based on the object dataset and the image.

EXAMPLE 11

The system of example 10, further comprising one or more optical fiducials positioned proximately to the patient anatomy, wherein the object described by the object dataset is the one or more optical fiducials.

EXAMPLE 12

The system of example 11, further comprising a patient tracking assembly positioned on the patient anatomy, wherein: (i) the patient tracking assembly comprises a position sensor of the one or more position sensors, (ii) the IGS navigation system is configured to update the location of the patient anatomy with the coordinate system based on movements of the position sensor, and (iii) the one or more optical fiducials are positioned on a surface of the patient tracking assembly.

EXAMPLE 13

The system of any one or more of examples 1 through 12, wherein the sensor comprises a camera positioned on the wearable frame and having an optical axis that is parallel to and statically offset from the neutral optical axis, and wherein the processor is further configured to, in addition to rendering the overlay image via the display: (i) receive an image from the camera and correlate the image to the overlay image based on a known static offset value, (ii) add the overlay image to the image to produce an augmented image, and (iii) display the augmented image on one or more displays other than the display.

EXAMPLE 14

The system of any one or more of examples 1 through 13, wherein: (i) the processor comprises one or more of a first processor of the IGS navigation system and a second processor of the HMD, (ii) the sensor comprises one or more of a gyroscope sensor coupled with the HMD, a camera mounted on the HMD, and a position sensor of the one or more position sensors mounted on the HMD, and (iii) the set of perspective data comprises one or more of a set of gyroscopic orientation data, a set of position coordinates associated with the coordinate system, a set of orientation coordinates associated with the coordinate system, and an image captured by the camera.

EXAMPLE 15

A method comprising: (a) configuring an image guided surgery ("IGS") navigation system to: (i) maintain a coordinate system corresponding to a tracked area, and (ii) track one or more position sensors with the coordinate system; (b) registering the location of a patient anatomy with the coordinate system; (c) receiving one or more correlated datasets, wherein each of the one or more correlated datasets comprise data associated with the coordinate system; (d) viewing the patient anatomy from a present perspective while wearing a head mounted display ("HMD") comprising a wearable frame and a display, wherein the display is positioned on the wearable frame to be intersected by a neutral optical axis of the wearer; (e) determining an orientation of the neutral optical axis relative to a viewed point on the patient anatomy based on a set of perspective data received from a sensor of the HMD; (f) determining a distance between an origin of the neutral optical axis and the viewed point based on the set of perspective data; (g) transforming the one or more correlated datasets based on the orientation and the distance to produce an overlay image that corresponds to the patient anatomy at the present perspective; and (h) rendering the overlay image via the display.

EXAMPLE 16

The method of example 15, wherein receiving the one or more correlated datasets comprises: (i) receiving a surgical path indicating a planned route of a surgical instrument within the patient anatomy, (ii) receiving a distal tip location indicating the current location of a distal tip associated with a position sensor of the one or more position sensors, and (iii) receiving an image slice selected from a set of preoperative images of the patient anatomy.

EXAMPLE 17

The method of any one or more of examples 15 through 16, wherein the sensor comprises a camera positioned on the wearable frame and having an optical axis that is parallel to and statically offset from the neutral optical axis, the method further comprising: (a) placing a patient tracking assembly on the patient anatomy, wherein the patient tracking assembly comprises: (i) a position sensor of the one or more position sensors, and (ii) one or more optical fiducials; (b) storing an object dataset that indicates one or more visible characteristics of the one or more optical fiducials and indicates a relationship between the one or more optical fiducials and the viewed point within the coordinate system; (c) receiving an image from the camera that contains the one or more optical fiducials; and (d) determining the orientation and the distance based on the object dataset and the image.

EXAMPLE 18

The method of example 17, wherein the sensor comprises a second position sensor of the one or more position sensors, further comprising determining the orientation and the distance based on the object dataset, the image, and the coordinate system.

EXAMPLE 19

A system for ENT visualization comprising: (a) an image guided surgery ("IGS") navigation system operable to: (i) maintain a coordinate system corresponding to a tracked area, (ii) track one or more position sensors with the coordinate system, and (iii) register the location of a patient anatomy with the coordinate system; (b) a hand-held display ("HHD") comprising a camera and a display; (c) a sensor operable to produce a set of perspective data indicating the perspective of the HHD relative to the patient anatomy; and (d) a processor; wherein the processor is configured to: (i) receive one or more correlated datasets, wherein each of the one or more correlated datasets comprise data associated with the coordinate system, (ii) while the HHD is directed at the patient anatomy from a present perspective, receive an image from the camera, (iii) determine an orientation of an optical axis of the camera relative to a viewed point on the patient anatomy based on the set of perspective data, (iv) determine a distance between an origin of the optical axis and the viewed point based on the set of perspective data, (v) transform the one or more correlated datasets based on the orientation and the distance to produce an overlay image that corresponds to the patient anatomy in the image, and (vi) display an augmented image via the display based on the overlay image and the image.

EXAMPLE 20

The system of example 19, wherein: (i) the sensor is a position sensor of the one or more position sensors, (ii) a second position sensor of the one or more positions sensors is positioned on the patient anatomy, and (iii) the one or more correlated datasets comprise: (A) a surgical path indicating a planned route of a surgical instrument within the patient anatomy, and (B) a distal tip location indicating the current location of a distal tip associated with a third position sensor of the one or more position sensors.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or high density polyethylene bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system for ear, nose, and throat ("ENT") visualization comprising:

(a) an image guided surgery ("IGS") navigation system operable to:

(i) maintain a coordinate system corresponding to a tracked area, the coordinate system being based on an electromagnetic field, (ii) track a plurality of position sensors with the coordinate system, and (iii) register a location of a patient anatomy with the coordinate system;

(b) a head mounted display ("HMD") comprising a wearable frame and a display, the display being positioned on the wearable frame and configured to be intersected by a neutral optical axis of a wearer;

(c) a sensor operable to produce a set of perspective data indicating the perspective of the HMD relative to the patient anatomy;

(d) a patient tracking assembly including (i) a disposable portion having a base configured to be attached to a patient's head of the patient anatomy and a coupling block secured to the base and (ii) a reusable portion having a coupling assembly including a latch configured to secure to the coupling block of the disposable portion and including a patient anatomy position sensor of the plurality of position sensors, the IGS navigation system being configured to update the location of the patient anatomy with the coordinate system based on signals from the patient anatomy position sensor; and (e) a processor configured to:

(i) receive one or more correlated datasets, each of the one or more correlated datasets comprising data associated with the coordinate system including a distal tip location indicating the current location of a distal tip of an instrument, the distal tip location data being acquired from an instrument position sensor of the plurality of position sensors, the instrument position sensor being positioned at the distal tip of the instrument, (ii) while the patient anatomy is viewed from a present perspective, determine an orientation of the neutral optical axis relative to a viewed point on the patient anatomy based on the set of perspective data, determine a distance between an origin of the neutral optical axis and the viewed point based on the set of perspective data, (iii) transform the one or more correlated datasets based on the orientation and the distance to produce an overlay image that corresponds to the patient anatomy at the present perspective, (iv) render the overlay image, including a live view of the current location of the distal tip having the instrument position sensor, via the display, and (v) drive a plurality of field generators to generate alternating electromagnetic fields and process signals from a navigation guidewire such that the processor is configured to track the live location of the navigation guidewire, the navigation guidewire including a guidewire position sensor of the plurality of position sensors that is responsive to positioning within the alternating electromagnetic fields generated by the plurality of field generators.

2. The system of claim 1, the one or more correlated datasets further comprising a surgical path indicating a planned route of a surgical instrument within the patient anatomy.

3. The system of claim 2, the one or more correlated datasets further comprising an image slice selected from a set of preoperative images of the patient anatomy.

4. The system of claim 1, the sensor being mounted on the HMD and being one of the plurality of position sensors, and the processor being further configured to, when determining the orientation of the neutral optical axis relative to the viewed point:

(i) determine an orientation of the neutral optical axis based on the coordinate system, (ii) determine an orientation of the patient anatomy based on the coordinate system, and (iii) correlate the orientation of the neutral optical axis and the orientation of the patient anatomy based on the coordinate system.

5. The system of claim 1, the sensor being mounted on the HMD and is one of the plurality of position sensors, and the processor being further configured to, when determining the distance between the origin and the viewed point:

(i) determine a location of the origin based on the coordinate system, (ii) determine the location of the patient anatomy based on the coordinate system, and (iii) determine the distance between the location of the origin and the location of the patient anatomy based on the coordinate system.

6. The system of claim 1, the processor being further configured to, when transforming the one or more correlated datasets:

(i) determine a scaling factor based on the distance between the origin and the viewed point, (ii) determine a perspective transform based on the orientation of the neutral optical axis relative to the viewed point, and (iii) produce an overlay image comprising a scale determined by the scaling factor and a perspective determined by the perspective transformation.

7. The system of claim 6, the display comprising a transparent screen, and the processor being further configured to render the overlay image on the transparent screen such that the overlay image appears on a directly viewed portion of the patient anatomy.

8. The system of claim 1, the processor being further configured to:

(i) repeatedly redetermine the distance and the orientation, and (ii) update and render the overlay image via the display as the distance and orientation change.

9. The system of claim 1, the sensor comprising a camera positioned on the wearable frame and having an optical axis that is parallel to and statically offset from the neutral optical axis, and the processor being further configured to, when determining the orientation and the distance:

(i) store an object dataset that indicates one or more visible characteristics of an object and indicates a relationship between the object and the viewed point, the viewed point having a tracked position, within the coordinate system, (ii) receive an image from the camera that contains the object, and (iii) determine the orientation and the distance based on the object dataset and the image.

10. The system of claim 1, the sensor comprising a camera positioned on the wearable frame and having an optical axis that is parallel to and statically offset from the neutral optical axis, and the processor being further configured to, in addition to rendering the overlay image via the display:

(i) receive an image from the camera and correlate the image to the overlay image based on a known static offset value, (ii) add the overlay image to the image to produce an augmented image, and (iii) display the augmented image on one or more displays other than the display.

11. The system of claim 1, wherein:

(i) the processor comprising one or more of a first processor of the IGS navigation system and a second processor of the HMD, (ii) the sensor comprising one or more of a gyroscope sensor coupled with the HMD, a camera mounted on the HMD, and an HMD position sensor of the plurality of position sensors mounted on the HMD, and (iii) the set of perspective data comprises one or more of a set of gyroscopic orientation data, a set of position coordinates associated with the coordinate system, a set of orientation coordinates associated with the coordinate system, and an image captured by the camera.

12. A system for ear, nose, and throat ("ENT") visualization comprising:

(a) an image guided surgery ("IGS") navigation system operable to:

(i) maintain a coordinate system corresponding to a tracked area, the coordinate system being based on an electromagnetic field, (ii) track a plurality of position sensors with the coordinate system, and (iii) register a location of a patient anatomy with the coordinate system;

(b) a head mounted display ("HMD") comprising a wearable frame and a display, the display being positioned on the wearable frame and configured to be intersected by a neutral optical axis of a wearer;

(c) a sensor operable to produce a set of perspective data indicating the perspective of the HMD relative to the patient anatomy;

(d) a patient tracking assembly including (i) a disposable portion having a base configured to be attached to a patient's head of the patient anatomy and a coupling block secured to the base and (ii) a reusable portion having a coupling assembly including a latch configured to secure to the coupling block of the disposable portion and including a patient anatomy position sensor of the plurality of position sensors, the IGS navigation system being configured to update the location of the patient anatomy with the coordinate system based on signals from the patient anatomy position sensor; and (e) a processor configured to:

(i) receive one or more correlated datasets from the patient anatomy position sensor, each of the one or more correlated datasets comprising data associated with the coordinate system, (ii) while the patient anatomy is viewed from a present perspective, determine an orientation of the neutral optical axis relative to a viewed point on the patient anatomy based on the set of perspective data, (iii) determine a distance between an origin of the neutral optical axis and the viewed point based on the set of perspective data, (iv) transform the one or more correlated datasets based on the orientation and the distance to produce an overlay image that corresponds to the patient anatomy at the present perspective, (v) render the overlay image, including a live view of the current location of a portion of an instrument within the patient anatomy, the instrument having an instrument position sensor within the patient anatomy, the instrument position sensor being configured to generate a signal indicating a location of the portion of the instrument, the live view of the current location being based at least in part on a signal received from the instrument position sensor, the live view being rendered via the display, and (vi) drive a plurality of field generators to generate alternating electromagnetic fields and process signals from a navigation guidewire such that the processor is configured to track the live location of the navigation guidewire, the navigation guidewire including a guidewire position sensor of the plurality of position sensors that is responsive to positioning within the alternating electromagnetic fields generated by the plurality of field generators.

13. A system for ear, nose, and throat ("ENT") visualization comprising:

(a) an image guided surgery ("IGS") navigation system operable to:

(i) maintain a coordinate system corresponding to a tracked area, the coordinate system being based on an electromagnetic field, (ii) track one or more position sensors with the coordinate system, and (iii) register a location of a patient anatomy with the coordinate system;

(b) a head mounted display ("HMD") comprising a wearable frame and a display, the display being positioned on the wearable frame and configured to be intersected by a neutral optical axis of a wearer;

(c) a sensor operable to produce a set of perspective data indicating the perspective of the HMD relative to the patient anatomy, the sensor comprising a camera positioned on the wearable frame and having an optical axis that is parallel to and statically offset from the neutral optical axis;

(d) a patient tracking assembly including a (i) disposable portion having a base configured to be attached to a patient's head of the patient anatomy and a coupling block secured to the base and (ii) a reusable portion having a coupling assembly including a latch configured to secure to the coupling block of the disposable portion and including a patient anatomy position sensor, the IGS navigation system being configured to update the location of the patient anatomy with the coordinate system based on signals from the patient anatomy position sensor; and (e) a processor configured to:

(i) receive one or more correlated datasets, each of the one or more correlated datasets comprising data associated with the coordinate system, (ii) while the patient anatomy is viewed from a present perspective, determine an orientation of the neutral optical axis relative to a viewed point on the patient anatomy based on the set of perspective data, (iii) determine a distance between an origin of the neutral optical axis and the viewed point based on the set of perspective data, (iv) transform the one or more correlated datasets based on the orientation and the distance to produce one or more overlay images that correspond to the patient anatomy at the present perspective, (v) render the one or more overlay images via the display, (vi) receive an image from the camera and correlate the image to the one or more overlay images based on a known static offset value, (vii) add a set of overlay images from the one or more overlay images to the image to produce an augmented image, (viii) display the augmented image on one or more displays other than the display, and (ix) drive a plurality of field generators to generate alternating electromagnetic fields and process signals from a navigation guidewire such that the processor is configured to track the live location of the navigation guidewire, the navigation guidewire including a guidewire position sensor of the plurality of position sensors that is responsive to positioning within the alternating electromagnetic fields generated by the plurality of field generators.

14. The system of claim 13, further comprising an HMD position sensor operable to produce an additional set of perspective data indicating the perspective of the HMD relative to the patient anatomy, in addition to the perspective data provided by the camera on the wearable frame, the additional set of perspective data being based on magnetic tracking of the HMD position sensor by the IGS navigation system.

15. The system of claim 13, the processor being configured to determine the distance between an origin of the neutral optical axis and the viewed point based on the set of perspective data and in correspondence with determining the orientation of the neutral optical axis relative to the viewed point on the patient anatomy.

* * * * *